United States Patent

Yoshida

[11] Patent Number: 5,994,572
[45] Date of Patent: Nov. 30, 1999

[54] PROCESS FOR PRODUCTION OF 1-ALKOXY-1-TRIMETHYLSILYLOXY CYCLOPROPANES

[75] Inventor: Yasuo Yoshida, Shizuoka-ken, Japan

[73] Assignee: Ihara Chemical Industry Co., Ltd, Tokyo, Japan

[21] Appl. No.: 09/117,390

[22] PCT Filed: Dec. 19, 1997

[86] PCT No.: PCT/JP97/04705

§ 371 Date: Jul. 29, 1998

§ 102(e) Date: Jul. 29, 1998

[87] PCT Pub. No.: WO98/28309

PCT Pub. Date: Jul. 2, 1998

[30] Foreign Application Priority Data

Dec. 20, 1996 [JP] Japan .................................. 8-354851

[51] Int. Cl.⁶ ........................................................ C07F 7/08
[52] U.S. Cl. ............................................................ 556/446
[58] Field of Search ............................................... 556/446

[56] References Cited

U.S. PATENT DOCUMENTS 5,412,134  5/1995  Singh et al. ............................ 556/437

FOREIGN PATENT DOCUMENTS 0 284 473 A1   9/1988   European Pat. Off. .
63-313792     12/1988   Japan .

OTHER PUBLICATIONS

Salaün et al; "Cyclopropanone Ethyl Hemiacetal from Ethyl 3–Chloropropanoate"; J. Org. Synthesis; vol. 63, pp. 147–153 (1984).

*Primary Examiner*—Paul F. Shaver
*Attorney, Agent, or Firm*—Kubovcik & Kubovcik

[57] ABSTRACT

The present invention provides a process for producing 1-alkoxy-1-trimethylsilyloxycyclopropane represented by the following general formula:

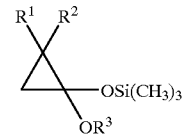

by reacting microgranular metallic sodium dispersed in a hydrocarbon solvent, β-halogenocarboxylic acid ester represented by the following general formula:

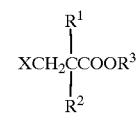

and chlorotrimethylsilane.

According to the present invention, by using no ether compound solvent (the ether compound solvent has various problems in safety) and using microgranular metallic sodium dispersed in a hydrocarbon solvent, 1-alkoxy-1-trimethylsilyloxycyclopropane can be industrially produced simply (no special apparatus is required) at an advantageous cost at a yield at least equal to that obtained when an ether is used as solvent.

2 Claims, No Drawings

PROCESS FOR PRODUCTION OF 1-ALKOXY-1-TRIMETHYLSILYLOXY CYCLOPROPANES

TECHNICAL FIELD

The present invention relates to a process for producing 1-alkoxy-1-trimethylsilyloxycyclopropane which is useful as an intermediate for medicines, an intermediate for agricultural chemicals, or an intermediate for production of perfumes, etc.

BACKGROUND ART

1-Alkoxy-1-trimethylsilyloxycyclopropanes are known to be an important raw material used in synthesis of N-cyclopro-pylamines which are raw materials in synthesis of medicines and agricultural chemicals (Chem. Comm., 1987, p. 897; Tetrahedron Lett., 1995, p. 7399). Since showing a very characteristic reactivity of homoenolate anion equivalent in a carbon-carbon bond-forming reaction, they are also known to become an important intermediate in synthesis of perfumes, etc. (J. Amer. Chem. Soc., Vol. 108, p. 3745, 1986).

As to the process for synthesis of 1-alkoxy-1-trimethylsilyloxycyclopropane, a process is well known which comprises reacting 3-chloropropionic acid ester with sodium sand in the presence of trimethylchlorosilane in an ether solvent (Org. Synthesis, Vol. 63, p. 147, 1984).

The process, however, has a problem of complicated operation such as the following. That is, metallic sodium is heat-melted in toluene or xylene and stirred, followed by cooling to form sodium sand; only the supernatant portion of the solvent is taken out; the residual metallic sodium is washed a plurality of times to change the solvent to ether. Further, the above process can be conducted in a laboratory flask but has been difficult to carry out on an industrial scale for the following reasons, for example. In this procedure, metallic sodium catches fire easily when water comes in; and the ether used as a reaction solvent has a low flash point and is difficult to recycle, and when the ether is used in a large amount, it easily forms a peroxide which is explosive.

Meanwhile, it is described in Synlett, p. 89, 1990 that the above reaction, when an ultrasonic is applied to the reaction system, proceeds without making metallic sodium as sand-like one by heat-melting or the like. However, use of ultrasonic in industrial production requires a special apparatus, which is disadvantageous in cost and not practically suitable for industrial production.

DISCLOSURE OF THE INVENTION

The object of the present invention is to provide a process for producing 1-alkoxy-1-trimethylsilyloxycyclopropane, which has industrial applicability and which is thoroughly satisfactory in yield, purity and cost.

The present inventors made a study in order to solve the above-mentioned problems of conventional laboratory processes for synthesis. As a result, the present inventors surprisingly found out that when microgranular metallic sodium dispersed in a hydrocarbon solvent (such sodium is easy to handle industrially) is used, industrial production of 1-alkoxy-1-trimethylsilyloxycyclopropane is possible, it is not necessary to use any ether solvent (the ether solvent has various problems in safety), the reaction proceeds sufficiently to a yield at least equal to that obtained when an ether solvent is used, and the production cost of intended product is favorable. The present invention has been completed based on the above finding.

The above object of the present invention has been achieved by providing a process for producing 1-alkoxy-1-trimethylsilyloxycyclopropane represented by the following general formula:

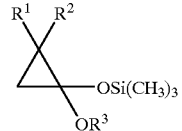

(wherein $R^1$ and $R^2$ are each independently a hydrogen atom or a lower alkyl group; $R^3$ is a lower alkyl group), by reacting microgranular metallic sodium dispersed in a hydrocarbon solvent, β-halogenocarboxylic acid ester represented the following general formula:

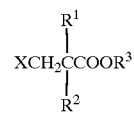

(wherein $R^1$, $R^2$ and $R^3$ are as defined above; and X is a halogen atom), and chlorotrimethylsilane.

BEST MODE FOR CARRYING OUT THE INVENTION

In the present invention, by using microgranular metallic sodium dispersed in a hydrocarbon solvent, the solvent used can be a hydrocarbon alone and no ether solvent is used which is usable in laboratory but whose use in industry is not preferred, and yet the reaction proceeds sufficiently to a yield at least equal to that obtained when an ether solvent is used. This characterizes the present invention. Hence, description is made first on the production of microgranular metallic sodium dispersed in a hydrocarbon solvent.

The microgranular metallic sodium dispersed in a hydrocarbon solvent, used in the present invention process can be obtained by heat-melting metallic sodium in a hydrocarbon solvent having a boiling point not lower than a melting point of metallic sodium, stirring the mixture at a high speed by the use of an appropriate micronizer, and allowing the resulting material to cool.

As the hydrocarbon solvent used above, there can be used at least one kind selected from aromatic hydrocarbons (e.g. toluene, xylene, mesitylene, ethylbenzene and isopropylbenzene), straight chain or branched hydrocarbons (e.g. n-octane, decane, dodecane and tridecane), alicyclic hydrocarbons (e.g. methylcyclohexane and ethylcyclohexane), bicyclic hydrocarbons (e.g. 1,2,3,4-tetrahydronaphthalene and decahydronaphthalene) and hydrocarbon mixtures [e.g. kerosene and Hisol (a trade name of high-boiling aromatic hydrocarbon compounds manufactured by Nippon Petrochemicals Co., Ltd.)], all having a boiling point not lower than a melting point of metallic sodium.

In the present invention process, use of an aromatic hydrocarbon solvent is preferred, and use of toluene or xylene is particularly preferred.

The amount of the hydrocarbon solvent used in micronization of metallic sodium can be set so that the weight of metallic sodium becomes 0.5 to 30%, preferably 1 to 10% based on the weight of the hydrocarbon solvent.

The particle diameter of the microgranular metallic sodium formed differs depending upon the stirring speed of the micronizer used, the shape of the stirrer used, the time of stirring employed, etc., but it can be controlled by changing these parameters. For use in the present invention process, microgranular metallic sodium having an average particle diameter of 80 μm or less is suitable. Particularly preferred is microgranular metallic sodium having an average particle diameter of 10 to 50 μm.

Therefore, there is no particular restriction as to the kind of the micronizer used, etc. as long as the above particle diameter of microgranular metallic sodium can be obtained.

In order to obtain such microgranular metallic sodium, addition of a small amount of a dispersant is effective. As a suitably usable dispersant, there can be mentioned saturated or unsaturated fatty acids having 10 to 20 carbon atoms, such as decanoic acid, lauric acid, palmitic acid, stearic acid, oleic acid, linoleic acid, linolenic acid and the like, and salts thereof such as sodium salt, potassium salt, barium salt, aluminum salt and the like. The amount of the dispersant used is 0.01 to 0.1% by weight, preferably 0.02 to 0.08% by weight based on the metallic sodium used.

In the present specification, the "average particle diameter" of microgranular metallic sodium refers to an average particle diameter obtained by placing a sample of the formed slurry of microgranular metallic sodium on a glass plate, taking a microphotograph thereof together with a scale or the like, measuring the diameters of about 2,000 to 2,500 particles of metallic sodium (the total particles contained in the photograph) in a predetermined direction using the scale, and calculating an average of all measurements. (Hereinafter, average particle diameter has the same meaning.)

Description is then made on the reaction between β-halogenocarboxylic acid ester and chlorotrimethylsilane.

In the present invention process, a reaction is allowed to take place between the microgranular metallic sodium dispersed in a hydrocarbon solvent, β-halogenocarboxylic acid ester represented by the above-mentioned general formula, and chlorotrimethylsilane.

The β-halogenocarboxylic acid ester used in the reaction is represented by the following general formul;

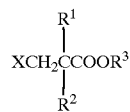

and can be an ester between a β-halogenocarboxylic acid (e.g. 3-chloropropionic acid, 2-methyl-3-chloropropionic acid, 2,2-dimethyl-3-chloropropionic acid, 3-bromopropionic acid, 2-methyl-3-bromopropionic acid, 2,2-dimethyl-3-bromopropionic acid, 3-iodopropionic acid, 2-methyl-3-iodopropionic acid or 2,2-dimethyl-3-iodopropionic acid) and a lower alcohol (e.g. methanol, ethanol, n-propanol, isopropanol, n-butanol or isobutanol). In the present specification, "lower" means that the substituent or compound appearing after the word has 1 to 4 carbon atoms.

In the above general formula, the substituents $R^1$ and $R^2$ are each independently a hydrogen atom, or a straight chain or branched lower alkyl group, and specific examples thereof are a methyl group, an ethyl group, an n-propyl group, an isopropyl group, an n-butyl group and an isobutyl group; the substituent $R^3$ is a straight chain or branched lower alkyl group, and specific examples thereof are a methyl group, an ethyl group, an n-propyl group, an isopropyl group, an n-butyl group and an isobutyl group; and the substituent X is a halogen atom, and specific examples thereof are a chlorine atom, a bromine atom, an iodine atom and a fluorine atom.

Specific examples of the β-halogenocarboxylic acid ester having the above substituents, usable in the present invention process are methyl 3-chloropropionate, ethyl 3-chloropropionate, n-propyl 3-chloropropionate, isopropyl 3-chloropropionate, n-butyl 3-chloropropionate, isobutyl 3-chloropropionate, methyl 2-methyl-3-chloropropionate, ethyl 2-methyl-3-chloropropionate, n-propyl 2-methyl-3-chloropropionate, isopropyl 2-methyl-3-chloropropionate, methyl 2,2-dimethyl-3-chloropropionate, ethyl 2,2-dimethyl-3-chloropropionate, n-propyl 2,2-dimethyl-3-chloropropionate, isopropyl 2,2-dimethyl-3-chloropropionate, methyl 3-bromopropionate, methyl 2-methyl-3-bromopropionate, methyl 2,2-dimethyl-3-bromopropionate, methyl 3-iodopropionate methyl 2-methyl-3-iodopropionate and methyl 2,2-dimethyl-3-iodopropionate. Of these, preferred are methyl 3-chloropropionate, ethyl 3-chloropropionate, n-propyl 3-chloropropionate, isopropyl 3-chloropropionate, methyl 2-methyl-3-chloropropionate, ethyl 2-methyl-3-chloropropionate, n-propyl 2-methyl-3-chloropropionate, isopropyl 2-methyl-3-chloropropionate, methyl 2,2-dimethyl-3-chloropropionate, ethyl 2,2-dimethyl-3-chloropropionate, n-propyl 2,2-dimethyl-3-chloropropionate and isopropyl 2,2-dimethyl-3-chloropropionate.

The microgranular metallic sodium used in the above reaction can be one produced as mentioned above. The use amount thereof is 1.9 to 2.5 moles, preferably 2.0 to 2.1 moles per mole of the β-halogenocarboxylic acid ester represented by the above general formula. It is preferred that no metallic sodium remains at the completion of the reaction in view of the prevention of product decomposition and the safety of post-treatment.

The use amount of chlorotrimethylsilane $ClSi(CH_3)_3$ in the above reaction is 0.8 to 1.1 moles, preferably 0.9 to 1.0 mole per mole of the β-halogenocarboxylic acid ester represented by the above general formula.

As to the reaction solvent, the hydrocarbon solvent used in production of microgranular metallic sodium can be used as it is. The use amount thereof is 200 to 3,000 ml, preferably 300 to 1,000 ml per mole of the β-halogenocarboxylic acid ester represented by the above general formula.

Needless to say, when the amount of the hydrocarbon solvent used in production of microgranular metallic sodium is larger or smaller than a level appropriate as the amount of the reaction solvent, adjustment is made so that the appropriate level is met.

The reaction temperature is −5 to 50° C., preferably 10 to 40° C.

As to the reaction pressure, there is no particular restriction, but atmospheric pressure is used ordinarily. After the completion of the reaction, the reaction mixture is subjected to filtration or distillation to remove the inorganic substances present in the reaction mixture; then, the resulting intended product, i.e. a 1-alkoxy-1-trimethylsilyloxycyclopropane is subjected to rectification and can be isolated at a high purity.

In the present invention process, by using the microgranular metallic sodium produced as above, the reaction proceeds sufficiently with only the hydrocarbon as the reaction solvent. This characterizes the present invention. In some cases, however, addition of an ether compound together with the hydrocarbon solvent gives an increased yield.

As the ether compound used for the above purpose, there can be mentioned, for example, diethyl ether, ethylene glycol dimethyl ether, diethylene glycol dimethyl ether and tetrahydrofuran. Of these, tetrahydrofuran is preferred. The amount of the ether compound used need not be a large amount unlike when it is used as a reaction solvent in conventional processes, and can be a small amount (5 to 50% by volume, preferably 10 to 30% by volume based on the hydrocarbon solvent used).

The present invention is described more specifically below by way of Examples and Comparative Examples.

EXAMPLE 1

T. K Homomixer M (a product of TOKUSYUKIKA Co. Ltd.) provided with a 500-ml four-necked flask having a valve at the bottom (T. K. Homomixer M is hereinafter referred to simply as "Homomixer") was fitted with a reflux condenser and a thermo-electric thermometer. Into the flask were placed 290 ml (251 g) of dehydrated toluene, 9.69 g (0.421 mole) of metallic sodium pieces and 4.9 mg (0.05% by weight based on metallic sodium) of aluminum stearate. While nitrogen was being blown into little by little from the bottom valve, the flask was heated by the use of a mantle heater. After the flask contents reached 100 to 105° C. and metallic sodium was melted, high-speed (7,500 to 8,000 rpm) stirring was conducted for 10 minutes by the use of Homomixer to micronize metallic sodium. Then, the heating was stopped and the flask contents were allowed to stand until they were cooled to room temperature, whereby was obtained a toluene dispersion of microgranular metallic sodium having an average particle diameter of 40 μm.

Then, while nitrogen was being blown into the flask to stir the flask contents, the metallic sodium dispersed in toluene was transferred into a 500-ml reaction flask by the use of a teflon tube. After the transfer, the flask contents were allowed to stand for a while to precipitate metallic sodium. 170 ml of the supernatant toluene was taken out by the use of a teflon tube. Then, the reaction flask was cooled with water. While stirring was being conducted in a nitrogen current, 21.7 g (0.2 mole) of trimethylchlorosilane was added dropwise at 15 to 17° C.

Then, the reaction mixture was heated to 30° C. with stirring. Thereto was dropwise added a solution of 27.3 g (0.2 mole) of ethyl 3-chloropropionate dissolved in 30 ml of toluene, at 30° C. in 2 hours with water-cooling. After the completion of the dropwise addition, stirring was conducted at the same temperature for 2 hours. To the resulting reaction mixture was added n-decane as an internal standard substance. The mixture was subjected to gas chromatography for quantitative analysis. As a result, 55.7% (0.1114 mole) of 1-ethoxy-1-trimethylsilyloxy cyclopropane was formed and 15.0% (0.030 mole) of ethyl 3-chloropropionate (raw material) remained. The selectivity from ethyl 3-chloropropionate to 1-ethoxy-1-trimethylsilyloxycyclopropane was 65.5%. Incidentally, the "selectivity" referred to in the present specification was calculated using the following formula.

Selectivity (%)=[amount of intended product (mole)]/{[fed amount of raw material (mole)]−[remaining amount of raw material (mole)]}×100

In the above formula, "raw material" refers to the β-halogenocarboxylic acid ester used.

EXAMPLE 2

The same operation as in Example 1 was conducted using 280 ml (242 g) of toluene, 14.57 g (0.633 mole) of metallic sodium pieces and 7.5 mg (0.05% by weight based on metallic sodium) of oleic acid, whereby was obtained a dispersion of microgranular (average particle diameter: 45 μm) metallic sodium. In the same manner as in Example 1, the dispersion of metallic sodium was transferred into a 500-ml reaction flask and allowed to stand therein. 100 ml of the supernatant toluene was taken out. The residue was subjected to the same operation as in Example 1, using 32.6 g (0.3 mole) of trimethylchlorosilane and a solution of 45.2 g (0.3 mole) of isopropyl 3-chloropropion ate dissolved in 45 ml of toluene, to give rise to a reaction.

The reaction mixture was analyzed by gas chromatography. As a result, 80.8% (in terms of ratio to total area) of 1-isopropoxy-1-trimethylsilyloxycyclopropane was formed and 3.0% of isopropyl 3-chloropropionate (raw material) remained. The inorganic salt which precipitated in the reaction, was removed by filtration, and the filtrate was subjected to rectification to obtain 34.3 g (yield: 60.7%) of 1-isopropoxy-1-trimethylsilyloxycyclopropane (boiling point: 56 to 59° C. at 15 mmHg).

EXAMPLE 3

The same operation as in Example 1 was conducted using 280 ml (197 g) of dehydrated n-octane, 9.73 g (0.423 mole) of metallic sodium pieces and 5.9 mg (0.06% by weight based on metallic sodium) of oleic acid, whereby was obtained a dispersion of microgranular (average particle diameter: 33 μm) metallic sodium. In the same manner as in Example 1, the dispersion of metallic sodium was transferred into a 500-ml reaction flask and allowed to stand therein. 105 ml of the supernatant n-octane was taken out, and the solvent amount was adjusted to 875 ml per mole of ethyl 3-bromopropionate to be added. Then, the resulting material was cooled to 5° C. Thereto was dropwise added 21.7 g (0.2 mole) of trimethylchlorosilane with stirring. After the completion of the dropwise addition, the resulting mixture was heated to 35° C. on a hot water bath. Thereto was dropwise added 36.2 g (0.2 mole) of ethyl 3-bromopropionate in small portions.

When heat generation took place and a reaction started, the mixture was cooled with water to keep the temperature at 35–40° C. The dropwise addition was completed in 2 hours. After the completion of the dropwise addition, the reaction mixture was again heated on a hot water bath and stirred at 35° C. for 1 hour. At the completion of a reaction, the reaction mixture was analyzed by gas chromatography. As a result, 56.4% (in terms of ratio to total area) of 1-ethoxy-1-trimethylsilyloxycyclopropane was formed and ethyl 3-bromopropionate (raw material) was completely consumed.

EXAMPLE 4

Homomixer provided with a 500-ml four-necked flask having a valve at the bottom was fitted with a reflux condenser and a thermoelectric thermometer. Into the flask were placed 290 ml (251 g) of dehydrated toluene, 9.69 g (0.421 mole) of metallic sodium pieces and 4.9 mg (0.05% by weight based on metallic sodium) of aluminum stearate. While nitrogen was being blown into little by little from the bottom valve, the flask was heated by the use of a mantle heater. After the flask contents reached 100 to 105° C. and metallic sodium was melted, high-speed (7,500 to 8,000 rpm) stirring was conducted for 10 minutes by the use of Homomixer to micronize metallic sodium. Then, the heating was stopped and the flask contents were allowed to stand until they were cooled to room temperature, whereby was obtained a toluene dispersion of microgranular metallic sodium having an average particle diameter of 40 μm.

Then, while nitrogen was being blown into the flask to stir the flask contents, the metallic sodium dispersed in toluene was transferred into a 500-ml reaction flask by the use of a teflon tube. After the transfer, the flask contents were allowed to stand for a while to precipitate metallic sodium. 170 ml of the supernatant toluene was taken out by the use of a teflon tube. Then, the reaction flask was cooled with water and 30 ml of dehydrated tetrahydrofuran was added. While stirring was being conducted in a nitrogen current, 21.7 g (0.2 mole) of trimethylchlorosilane was added dropwise at 15 to 17° C.

Then, the reaction mixture was heated to 30° C. with stirring. Thereto was dropwise added a solution of 24.6 g (0.18 mole) of ethyl 3-chloropropionate dissolved in 30 ml of toluene, at 30° C. in 2 hours with water-cooling. After the completion of the dropwise addition, stirring was conducted at the same temperature for 2 hours. To the resulting reaction mixture was added n-decane as an internal standard substance. The mixture was subjected to gas chromatography for quantitative analysis. As a result, the selectivity from ethyl 3-chloropropionate to 1-ethoxy-1-trimethylsilyloxycyclopropane was 74.4% and ethyl 3-chloropropionate (raw material) was consumed completely.

EXAMPLE 5

Using 280 ml (242 g) of toluene, 14.5 g (0.63 mole) of metallic sodium pieces and 7.3 mg (0.05% by weight based on the metallic sodium) of aluminum stearate, the same operation as in Example 1 was conducted to form microgranular (average particle diameter: 30 μm) metallic sodium. The microgranular metallic sodium was precipitated; the supernatant toluene was taken out and the amount of toluene was adjusted to 100 ml; and 30 ml of tetrahydrofuran and 32.6 g (0.3 mole) of trimethylchlorosilane were added dropwise. Using a solution of 41.0 g (0.3 mole) of ethyl 3-chloropropionate dissolved in 50 ml of toluene, the same operation as in Example 1 was conducted to give rise to a reaction.

To the reaction mixture was added n-decane as an internal standard substance, and gas chromatography was conducted for quantitative analysis. As a result, the amount of formed 1-ethoxy-1-trimethylsilyloxycyclopropane was 68.6% and the amount of remaining ethyl 3-chloropropionate was 12.0%. The selectivity from ethyl 3-chloropropionate to the intended product was 78.0%. The reaction mixture was subjected to suction filtration in a nitrogen atmosphere, and the filtrate was subjected to rectification under reduced pressure. After the initial distillate, i.e. the low-boiling substances (e.g. tetrahydrofuran) and the solvent (toluene) were recovered, there was obtained 34.1 g (yield: 65.2%) of 1-ethoxy-1-trimethylsilylo xycyclopropane (boiling point: 74 to 75° C. at 65 mmHg).

EXAMPLE 6

Using 300 ml (260 g) of toluene, 4.86 g (0.211 mole) of metallic sodium pieces and 2.4 mg of aluminum stearate, the same operation as in Example 1 was conducted to form microgranular (average particle diameter: 30 μm) metallic sodium. The microgranular metallic sodium was precipitated; the supernatant toluene was taken out and the amount of toluene was adjusted to 50 ml; and 15 ml of tetrahydrofuran and 10.9 g (0.1 mole) of trimethylchlorosilane were added dropwise. By dropwise adding a solution of 13.7 g (0.1 mole) of ethyl 3-chloropropiona te dissolved in 15 ml of toluene, a reaction was allowed to take place.

To the reaction mixture was added n-decane as an internal standard substance, and gas chromatography was conducted for quantitative analysis. As a result, the amount of formed 1-ethoxy-1-trimethylsilyloxycyclopropane was 71.2% and the amount of remaining ethyl 3-chloropropionate was 18.0%. The selectivity from ethyl 3-chloropropionate to the intended product was 86.8%.

EXAMPLE 7

A reaction was conducted in the same manner as in Example 4 except that 24.6 g (0.18 mole) of ethyl 3-chloropropionate was replaced by 24.5 g (0.2 mole) of methyl 3-chloropropionate. After the completion of the reaction, the reaction mixture was analyzed. As a result, the amount of formed 1-methoxy-1-trimethylsilyloxycyclopropane was 77.8% by gas chromatography (ratio to total area). The reaction mixture was subjected to suction filtration in a nitrogen atmosphere, and the filtrate was subjected to rectification under reduced pressure to obtain 23.4 g (yield: 73.0%) of 1-methoxy-1-trimethylsilyloxycyclopropane (boiling point: 40 to 42° C. at 28 mmHg).

EXAMPLE 8

A reaction was conducted in the same manner as in Example 4 except that 24.6 g (0.18 mole) of ethyl 3-chloropropionate was replaced by 30.1 g (0.2 mole) of isopropyl 3-chloropropionate. After the completion of the reaction, the reaction mixture was analyzed. As a result, the amount of formed 1-isopropoxy-1-trimethylsilyloxycyclopropane was 79.1% by gas chromatography (ratio to total area). The reaction mixture was subjected to suction filtration in a nitrogen atmosphere, and the filtrate was subjected to rectification under reduced pressure to obtain 26.7 g (yield: 70.9%) of 1-isopropoxy-1-trimethyl silyloxycyclopropane (boiling point: 62 to 66° C. at 21 mmHg).

COMPARATIVE EXAMPLE 1

According to the method described in Org. Synthesis, Vol. 63, p. 147, a reaction was conducted by using sodium sand formed in a reaction flask and by changing the solvent used in formation of the sodium sand, to an ether (a reaction solvent). That is, 4.83 g (0.21 mole) of metallic sodium and 100 ml of toluene were fed into a 300-ml four-necked flask provided with a stirrer, a thermometer and a reflux condenser. Vigorous stirring was conducted in a nitrogen current at 900 to 1,000 rpm at 98 to 100° C. for 5 minutes, and the resulting mixture was allowed to stand and cool to room temperature to obtain sodium sand. Then, the supernatant toluene was taken out by the use of a teflon tube while nitrogen was being fed under pressure. To the remaining metallic sodium was added 60 ml of diethyl ether and then stirred, after which the supernatant was taken out in a similar manner. This washing operation was conducted two more times. Then, 100 ml of diethyl ether was added. Thereto was dropwise added 10.86 g (0.10 mole) of trimethylchlorosilane at 7 to 17.8° C. in a nitrogen current, with stirring.

The reaction mixture was heated to 25° C. with stirring. Thereto was slowly added dropwise a solution of 13.70 g (0.10 mole) of ethyl 3-chloropropionate dissolved in 30 ml of ether. When a reaction started and the system reached 30° C., the system was cooled on a water bath. The dropwise addition was continued for 2 hours at the same temperature.

After the completion of the dropwise addition, refluxing with heating was conducted for 1 hour. After the completion of the reaction, gas chromatography using n-decane as an internal standard substance was conducted for quantitative analysis. As a result, the amount of formed 1-ethoxy-1-trimethylsilyloxycyclopropane and its selectivity were both 60.5%. The raw material (ethyl 3-chloropropionate) was consumed completely.

COMPARATIVE EXAMPLE 2

An operation was conducted in the same manner as in Comparative Example 1 except that after a toluene dispersion of sodium sand was formed in a reaction flask, no solvent change to diethyl ether was conducted, 100 ml of the very toluene used in the formation of sodium sand was used as a reaction solvent, and a reaction was conducted by adding ethyl 3-chloropropionate in the form of a solution thereof in 30 ml of toluene. Gas chromatography was conducted using n-decane as an internal standard substance, for quantitative analysis. As a result, the amount of formed 1-ethoxy-1-trimeth-ylsilyloxycyclopropane and its selectivity were 49.7%. The raw material (ethyl 3-chloropr opionate) was consumed completely.

Industrial Applicability

The process of the present invention has enabled the production of 1-alkoxy-1-trimethylsilyloxycyclopropane without using any ether as solvent (ether solvent has various problems in safety, in industrial production) and by using microgranular metallic sodium dispersed in a hydrocarbon solvent usable in industry, at a yield at least equal to that obtained when an ether is used as solvent. The present process can produce 1-alkoxy-1-trimethylsilyloxycyclopropane simply without requiring any special apparatus (e.g. a ultrasonic generator), at an advantageous production cost, without using a complicated operation of solvent change; and has made possible industrial production of 1-alkoxy-1-trimethylsilyloxycyclopropane, which had been difficult based on conventional laboratory processes.

I claim:

1. A process for producing 1-alkoxy-1-trimethylsilyloxy cyclopropane represented by the following general formula:

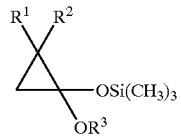

(wherein $R^1$ and $R^2$ are each independently a hydrogen atom or a lower alkyl group; $R^3$ is a lower alkyl group), by reacting microgranular metallic sodium dispersed in a hydrocarbon solvent, β-halogenocarboxylic acid ester represented by the following general formula:

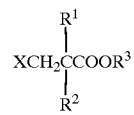

(wherein $R^1$, $R^2$ and $R^3$ are as defined above; and X is a halogen atom), and chlorotrimethylsilane.

2. A process for producing 1-alkoxy-1-trimethylsilyloxycyclopropane according to claim 1, wherein the microgranular metallic sodium has an average particle diameter of 80 μm or less.

* * * * *